(12) United States Patent
Lallemang

(10) Patent No.: US 8,196,824 B2
(45) Date of Patent: Jun. 12, 2012

(54) DETECTING COMPONENTS OF A MEDICAL DIAGNOSTIC SYSTEM RELATED DOCUMENTS

(75) Inventor: Marco Lallemang, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 724 days.

(21) Appl. No.: 12/047,937

(22) Filed: Mar. 13, 2008

(65) Prior Publication Data

US 2008/0230608 A1 Sep. 25, 2008

(30) Foreign Application Priority Data

Mar. 20, 2007 (DE) .......................... 10 2007 013 324

(51) Int. Cl.
*G06Q 30/00* (2012.01)
(52) U.S. Cl. ........................................ 235/385; 235/375
(58) Field of Classification Search .................. 235/385, 235/375; 705/34; 340/572.1
See application file for complete search history.

(56) References Cited

U.S. PATENT DOCUMENTS

| 6,092,722 | A | 7/2000 | Heinrichs et al. |
| 2006/0244593 | A1* | 11/2006 | Nycz et al. ................. 340/572.1 |
| 2006/0284730 | A1 | 12/2006 | Schmid et al. |
| 2007/0001839 | A1* | 1/2007 | Cambre et al. ........... 340/539.12 |
| 2008/0147056 | A1* | 6/2008 | van der Weide et al. ....... 606/33 |
| 2008/0147529 | A1* | 6/2008 | Kreiner et al. .................. 705/34 |
| 2008/0316045 | A1* | 12/2008 | Sriharto et al. .......... 340/825.49 |

FOREIGN PATENT DOCUMENTS

| DE | 196 29 646 A1 | 1/1998 |
| DE | 10 2005 022 347 A1 | 11/2006 |
| EP | 1 736 112 A1 | 12/2006 |

OTHER PUBLICATIONS

German Office Action dated Oct. 2007 (with attached English translation).

* cited by examiner

*Primary Examiner* — Ahshik Kim
(74) *Attorney, Agent, or Firm* — Lempia Summerfield Katz LLC

(57) ABSTRACT

A method for detecting installed or associated components that are each identified by at least one unique identifier is provided. The identifiers may be read out by at least one reader device. The identifiers, for detecting the respective components, are read out automatically by the reader device. All the serialized components of the system are identified and detected.

28 Claims, 2 Drawing Sheets

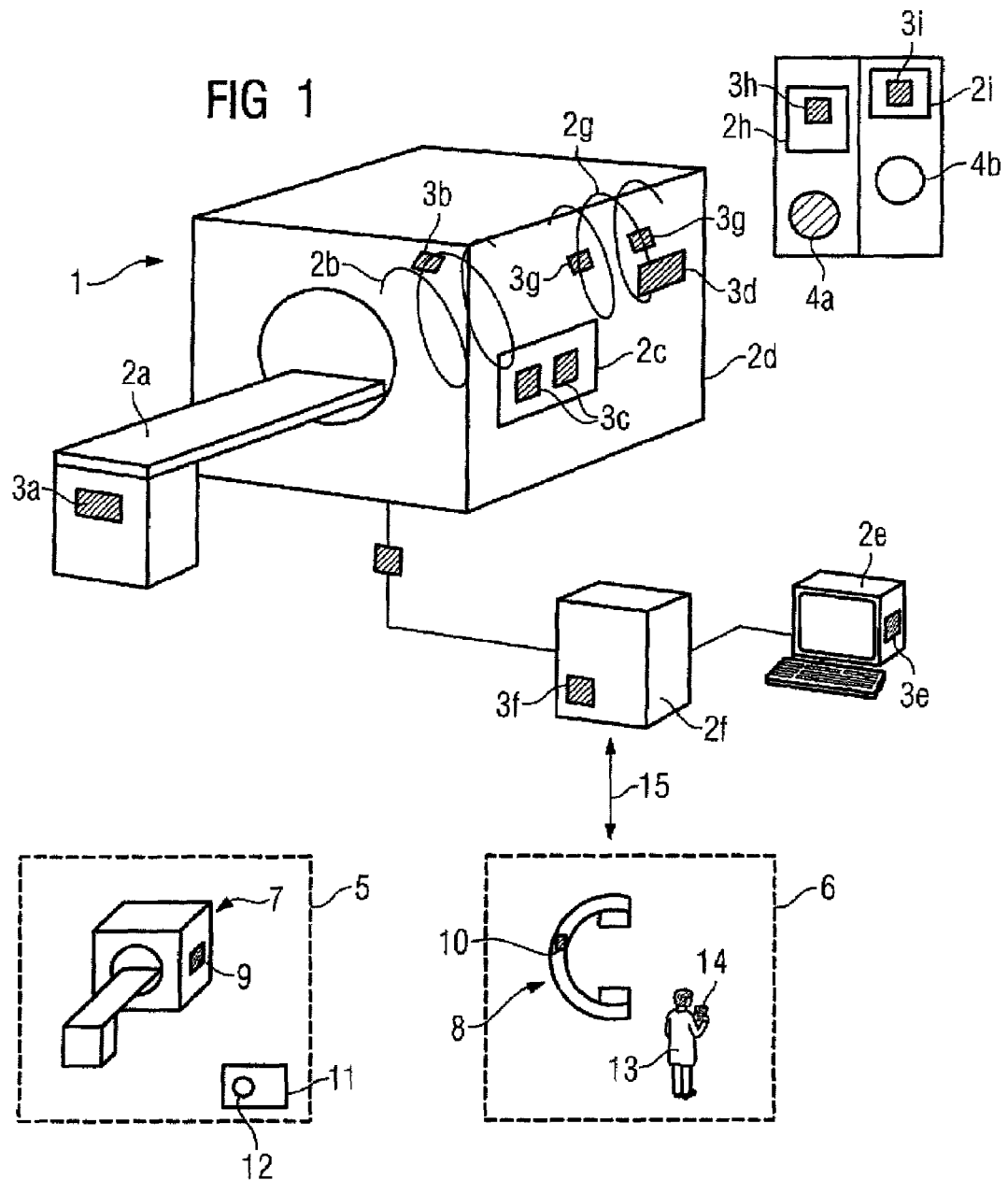

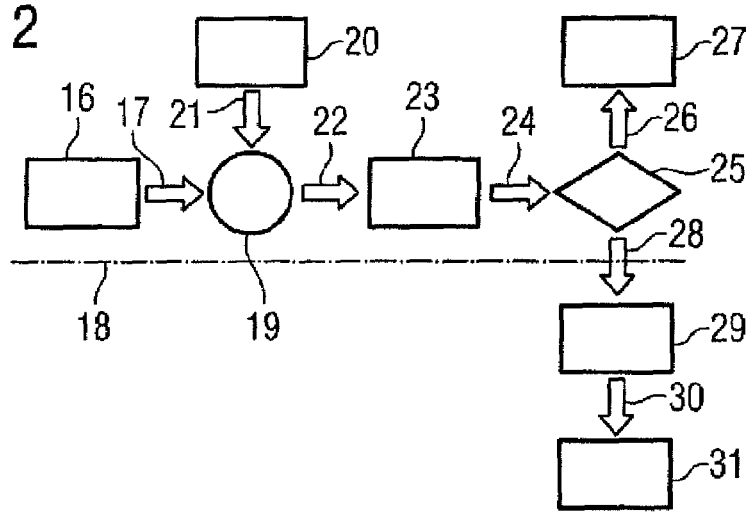
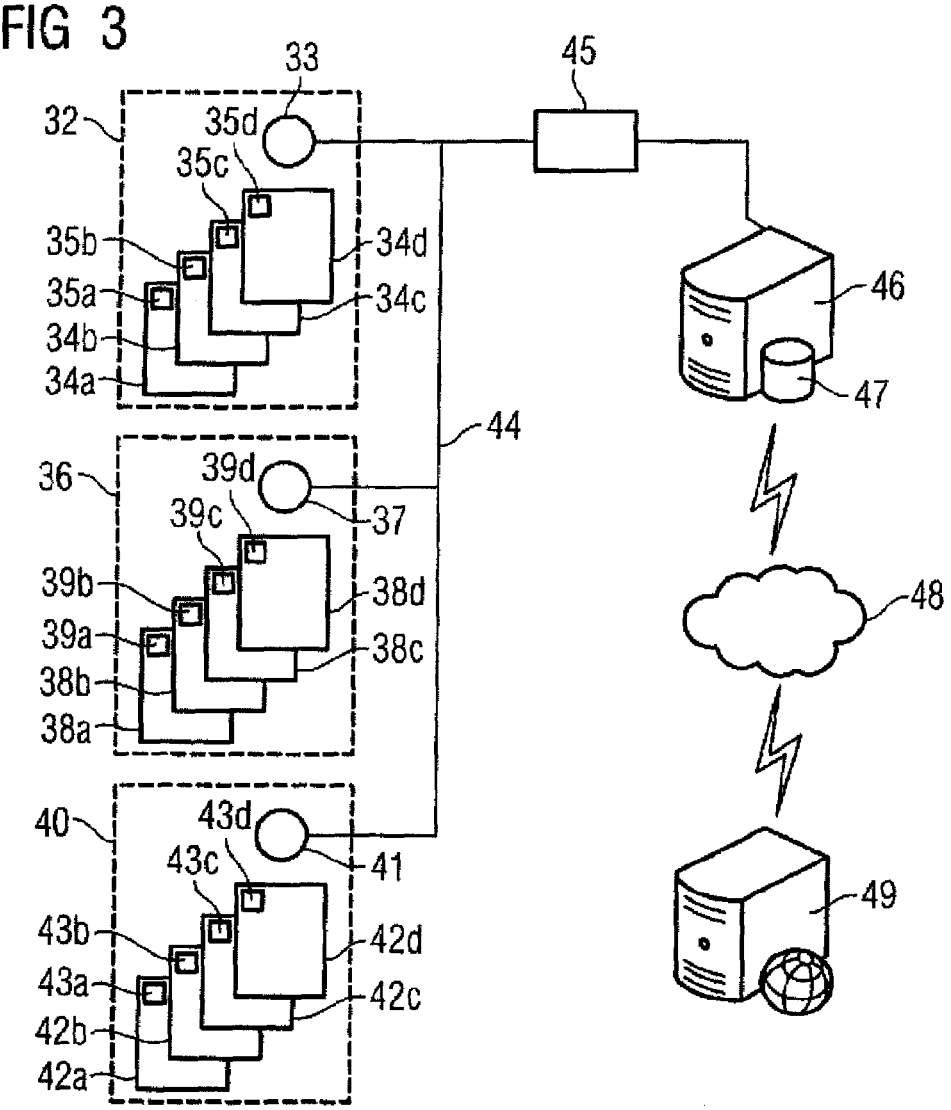

DETECTING COMPONENTS OF A MEDICAL DIAGNOSTIC SYSTEM RELATED DOCUMENTS

This application claims the benefit of German patent application DE 10 2007 013 324.5, filed on Mar. 20, 2007, which is incorporated herein by reference,

BACKGROUND

The present embodiments relate to a method for detecting installed or associated components of a medical diagnostic system. For example, components of a magnetic resonance system or MRI scanner are detected, In various medical diagnostic systems, such as magnetic resonance scanners, lists are used to check for higher-order functional units when the particular system is being put into operation. The feedback is done manually via an appropriate software interface. If it is necessary to replace individual components of the system, then in accordance with the same list-based method, only the higher-order units are manually detected and reported back.

Because of the numerous manual tasks required for this and because of the many interfaces, as well as the lack of comprehensive processing software suitable for detecting components and administering them, the type of feedback with regard to the components installed is at present quite flawed. Not all the components are detected. Only those components that have been defined as higher-order function units are detected. In addition, numerous manual processes are required, such as manual input that a component has been replaced. The input is done by the person who performed the replacement or by someone else who is responsible for keeping such information up to date in the pertinent software. A person may forget to do this inputting or may input incorrectly. Suitable lists of table calculations or web interfaces must be kept up to date manually by an administrator. This is a constant source of mistakes. It is not always assured that a system is in an authorized state at all times.

As a result, besides the occurrence of authorization problems, safety can be impaired. Technical reliability cannot be adequately assured.

From German Patent Disclosure DE 10 2005 022 347 A1, a basic medical system is known that is arranged for cooperating with a medical accessory component. The accessory component is assigned at least one point identification element, in which an identification element is stored in memory that relates to the medical accessory component.

In German Patent DE 196 29 646 C2, both a method and an apparatus for automatic identification of components in medical equipment systems are described. In endoscopy systems, a data storage medium that can be written into and read by a separate unit is provided in one component. The data storage medium stores parameters of at least that component. In a separate unit, at least one read/write control unit is provided for repetitively reading and writing of the data storage medium.

European Patent Disclosure EP 1 736 112 A1 relates to a medical device with a medical instrument that has a transponder. The transponder is removably secured to the device. The transponder acts as a data medium with regard to specific information on the medical instrument.

SUMMARY AND DESCRIPTION

Installed or system-associated components of a medical diagnostic system are detected. The components are each identified by at least one unique identifier. The identifier may be read out by at least one reader device or scanner. For detecting the respective component, this identifier is read out automatically by the reader device. All the components of the system may be identified and detected serially.

Components in medical diagnostic systems that are accordingly installed in medical diagnostic systems or associated in the broadest sense with these systems are detected. A medical diagnostic system is understood comprehensively to be a piece of medical equipment, for example, or a plurality of rooms with complex medical equipment, such as especially large equipment magnetic resonance scanners or computed tomography scanners. Large equipment systems may be formed in at least one room with corresponding components of electrical and mechanical kinds, such as magnetic resonance scanners. In such a system, it is important to be able to recognize the components reliably. Reliable recognition allows obtaining information as to whether this technologically complex system is in an authorized state and accordingly can be used without risk to a patient.

The serialized components, many components, or even all the components of the particular system are identified by identifiers. Under some circumstances, one component may have a plurality of identifiers. These identifiers can be read out by one or more reader devices. As a result of the readout of the identifier, reliable detection of the various components is accomplished.

Automatic detection of the components installed in the system is achieved. The basis is a suitable identifier mechanism installed in the system. A system of identifiers is provided.

If the components are provided with identifiers, then the components or the associated identifiers may be read out automatically by the reader device, regardless of whether the components are embodied as electrical or mechanical components. For greater safety, a readout can optionally be done multiple times, such as by a second or further reader device, so that the components are reliably detected in every case.

Increased efficiency is provided because there are fewer manual activities. Each component may be recognized. Because recognition is no longer limited to higher-order function units, a comprehensive detection of components is possible. An operator or administrator may not need to enter the individual components by hand into process software or the like. Faster, simpler, and error-free performance of the activities may be performed in the system. Both installation and maintenance may be done faster. The identified parts may be mapped and/or listed conveniently.

The automatic detection makes it possible, comparatively often and in real time, to update the data stored in memory. The data pertains to the system in view of the actual state of the installed basis. Decisions, such as decisions about retrofits, may be made on the basis of fact-based real-time data.

All the serialized components of the system may be identified and detected. If the system has many components, which as a rule would be the case, then it is appropriate for all the components of the system or at least those that have a serial number to be provided with an identifier and automatically detected. A comprehensive overview of the state of the system is obtained. Hence, particularly in conjunction with suitable software that performs such monitoring, it is possible quickly to tell whether the system is in the authorized state and accordingly whether its technological reliability can be guaranteed. For instance, it is also possible to tell whether only the original spare parts made by the manufacturer have been used or whether there are components in the system that were replaced without being monitored and that accordingly could be a safety risk for operation of the system.

At least one reader device is provided internally in the system. For instance, in a magnetic resonance scanner, a reader device can be provided in the appropriate control cabinets or cabinets for electronic components or in the one or more rooms of the system. Optionally, a plurality of reader devices may be present, such as a portable (mobile) reader device for an operator or a reader device permanently installed in a cabinet. Various identifiers may be optionally read out with the reader devices. Alternatively, the individual identifiers can be read out. If the reader device is permanently located in the system or is accessible in the area of the system, then the component detection is performed regardless of whether an administrator or a worker tasked with installing or maintaining the system is in the vicinity.

At least one identifier of one component may be read out automatically at defined times and/or as a function of certain events. For example, the identifier is read upon startup of the system and/or in conjunction with a repair, maintenance, and/or replacement of at least one component.

Automatic detection may be performed upon installation of the system or when changes are made in the system. The automatic readout of the identifier makes automatic detection of replaced components possible. If all the identifiers may be read out at certain events. For example, on installation, all the components are checked, or in repair or maintenance, all the system parts are detected in the context of the automatic readout.

By the automatic readout, for instance upon a component replacement, it can be assured that the system is still in an authorized state. Safety problems may be prevented.

The identifier or identifiers of a component may be read out by software stored in an internal and/or an external computation device. The reader device or reader devices are optionally triggered by the software, which controls the automatic readout of the identifiers by the reader devices. The outcomes of the reading out or the information stored in memories of the identifiers is forwarded via the reader devices to the software. The software processes the information, and thus the readout takes place using that information. For that purpose, the software may operate with a database system, in which further information is optionally stored in memory for certain identifiers. For example, information that a component associated with an identifier (for instance in the form of a number) was replaced or repaired at a certain time or the like is stored in the database. Optionally, the software procures on its own further information, for example, about a component newly added to the system via an intranet, the Internet, or some other data network. For example, a service provider or an external data base system provides the further information. For example, specifications can be called up using serial numbers.

The readout by the software may also be done from a different site. For example, it is possible for the status of the system to be monitored by a service provider or a data warehouse. The service provider monitors the status of the medical diagnostic system based on the readout of the identifiers with the aid of the on-site reader devices.

Mechanical and/or electrical components of the system may be detected. The capability of detecting all or a subset of the components of the system is provided. At least all the components that have a serial number, regardless of the type of component, may be detected.

Recourse to identifiers that are read out by reader devices is provided. Such identifiers may be attached to all the components, regardless of whether they are purely mechanical or electrical or electronic components. A suitably selected identifier assures correct reading without problems.

This represents a distinction from the conceivable possibility of providing electrical components with electrically erasable programmable read-only memories for identification purposes (ID-EEPROMs or ID electrically erasable programmable read-only memories). With such EEPROMs, while automatic recognition can be achieved, nevertheless this is limited to electrical or electronic components that are connected to a communications bus. By comparison, automatic detection of the electrical and mechanical components of the system may be possible.

At least one component may be identified by at least one identifier based on radio frequency identification and/or by an optically readable identifier. Radio frequency identification (RFID) makes it possible without problems to attach identifiers, which are embodied as labels or transponders, to all the components of a system. Attaching RFID tags to metal is possible as well. In the simplest case, the RFID labels are simply glued on. Other attachment options are possible.

The RFID identifier offers contactless readout, since the data transmission between the transponder and the reader device takes place via electromagnetic waves. The most various data can be stored in memory on RFID tags, thus including data that goes beyond a simple identifier in the form of a number or the like, for example. Additional information offers an alternative or supplement to software that has additional data in a database or that can access this king of (external) database.

In the case of optically readable identifiers, by comparison, view field contact is necessary. For that purpose, the reader device is more or less in the immediate vicinity of the identifier.

Moreover, other identifiers may be used. It is equally possible for components to be identified with various identifier methods or to have more than one identifier. A plurality of identifiers may be based on various principles. For example, for greater security, two RFID tags may be attached to one component. It is possible for an RFID tag to be combined with an optically readable identifier.

The identifier or identifiers may be read out with the aid of at least one reader device disposed in a cabinet and/or in a room in the system.

Suitable reader devices may be mounted on all or at least many of the cabinets and rooms in the system. For example, reader devices are placed in all the rooms in a nuclear medical facility. A nuclear medical facility my have rooms for X-ray machines, CT scanners, and the like. In that case, when the entire system or individual parts of it are started up, the components can be detected directly with the aid of the reader devices that are present directly on-site.

Alternatively, mobile or portable reader devices are brought on-site for reading out the identifiers of the components. Additional permanent reader devices may assure an automatic readout regardless of whether someone performing maintenance work, for example, has thought to bring a reader device with him.

At least one read-out or detected components may be administered by software stored in memory in an internal and/or external computation device.

For administration, the software may be coupled with a database system. Even retroactively, for example, many functions for the administration may be implemented in a comparatively simple way.

The software may already be provided in the system, for instance in a console for operating the individual items of equipment or in a computation device. Alternatively or in addition, the software may also or only be stored in memory on an external computation device, such as at a service provider or the manufacturer of the system or at a data warehouse in the central corporate network.

As the software or a component of the software, a database may be used. Optionally, further data associated with at least one identifier or a plurality of identifiers are previously stored in memory and/or are stored in memory by an operator and/or by automatic access to data sources. The database may be an extensible markup language-based database.

This database may be present locally or in the vicinity of the system. By the use of a defined format, such as XML (extensible markup language), it is assured that updating is possible without problems at all times. By way of a suitable remote connection of the local data base with a central data warehouse (in the corporate network or completely externally), the installed, recognized components may be forwarded. A connection of one local and one external database is also possible. To assure that data is kept up to date, an update of one or another database system is performed at regular intervals or when changes are made. This can be done automatically, controlled by a computation device or by software.

With the aid of the software, logging or tracing of at least one detected component can be made possible and/or can be done automatically. In the case of identifiers that enable a great deal of data to be stored in memory, this logging can also be done with the aid of the stored data, such as installation data. Advantageously, however, only the basic information, such as a number, is stored in memory in the identifier and is supplemented with suitable software information or data from an associated database. For example, when the component was installed, whether repairs might have been performed on it, or whether it is an original part, and the like can be stored in memory in the database. All the serialized parts of the installed basis may be optionally traced or logged.

In the software, after a replacement of at least one component, an operator may automatically be offered options and/or specifications for a setting and/or quality assurance of the component. The installed component, which replaces the original component, is accordingly automatically recognized by the automatic readout. For example, the next time the system is started up, whereupon setting options or expedient settings are indicated or specified via the interface of the software that guides the operator, using a suitable setup menu. Moreover, for example by the selection of a suitable menu point, an operator may perform a quality assurance of the component in order to tell whether the component is operating flawlessly, in particular in the context of the system with its many further components. To initiate a setting, all an operator may need to do is to provide a confirmation.

In the event of a later expansion of the system, options and/or specifications for a configuration, setting and/or quality assurance of at least one component and/or of the system may be offered and/or appropriate steps may be taken in the software as a function of a readout of identifiers.

Accordingly, the already existing components or newly installed components may be recognized as a function of an automatic readout of the identifications assigned to them. Configuration settings and the like for the components may be specified, or the configurations can be made directly. For example, upon a replacement of a gradient coil, monitoring of the gradient coil system in accordance with a suitable check protocol may optionally be proposed or performed automatically as a function of a readout of the identifier or identification of the new gradient coil. Setting options can also be furnished that are optionally adopted automatically after confirmation by a user.

Furthermore, in the software, at least one detected component and/or data associated with at least one identifier, in particular in the database that is optionally present, may be forwarded to a data warehouse. In a data warehouse, which may be associated with an external or central corporate network and which performs updating tasks, comparatively or constantly current data are available either when forwarding is done at regular intervals or upon each readout. A reliable overview about the status at the time of the locally present system is on hand in the central corporate network.

Moreover, a data warehouse connected to the software via a data connection or this kind of central data collection may bring about configuration-specific, adjustment-specific, and/or quality assurance-specific actions for at least one component and/or for the system. The actions are brought about as a function of a data comparison with recourse to the software. In a central data warehouse for the corporation or a data warehouse located at a service provider, a data comparison may be performed. The comparison is based on the data of the software and of the central collection. This data comparison can be used, in the context of an assessment, to ascertain whether one or more actions pertaining to the components or to the entire system are necessary. These actions, which are performed as a function of the data comparison based on the forwarded data, may pertain to the configuration of the system or may be steps to be performed in the field of quality assurance, such as the course or execution of a test protocol upon installation of a relevant new component. This can be done automatically, for example via a computation device, or operator-based.

With the aid of data forwarding, it is possible in a data warehouse to tell directly whether a component has been replaced. If a component has been replaced, suitable steps may be taken in order to assure that the system is, for example, still in an authorized state.

As a function of the detection of at least one component, system-specific decisions, such as retrofitting steps, may be made automatically and/or reinforced by an operator. Software stored in memory in an internal and/or external computation device may render the decision. For example, automatic detection of a component may show, and for this purpose supplementary information might optionally be procured from a database, that for safety reasons because of the long length of use of the component, a replacement is necessary or might at least be practical. Thereupon, a new component may be ordered automatically using software in a computation device. Beforehand, a report from an operator may optionally be requested to confirm such an ordering event. The software may access data that, for example, provides information about a plurality of detected components, such as whether they are compatible with one another given the current knowledge base. If the components are not compatible, then a replacement of the affected components may be recommended to improve the safety of the system. These decisions may optionally be made by administration and/or readout software.

A medical diagnostic system, in particular a magnetic resonance scanner, has a plurality of components. The components are for performing the method as described herein. This medical diagnostic system has a plurality of components each identified with at least one unique identifier. The identifier may be read out by at least one reader device. The identifiers may be read out automatically by the reader device serially to detect the components with all the components in the system being identified and detectable.

The medical diagnostic system accordingly has a plurality of components that are also identified and whose identifiers can be read out automatically by a reader device in the system or a reader device carried by an operator. Read out is performed at a system startup or when a component or components are replaced. In addition, for mere detection, recourse may be had to further data, stored in memory in a database or on the components in order to obtain information about the status of the system, such as installation or replacement data.

Moreover, all the serialized components of the system are identified and detectable. It is thus possible to gain a complete overview of the current status of the medical diagnostic system by way of detecting the components.

The system may furthermore have at least one reader device embodied for automatic readout of identifiers. This reader device may be integrated in rooms or cabinets, such as control cabinets, of the medical diagnostic system. It may also be a mobile or portable reader device associated with the system but that can also be removed from the rooms of the system.

At least one identifier of one component may be automatically read out by the at least one reader device at defined times and/or as a function of certain events. For example, read out occurs upon startup of the system and/or in conjunction with a repair, maintenance, and/or replacement of the component or another component.

The identifier or the plurality of identifiers is read out in the medical diagnostic system, particularly upon startup of the system or after component replacement or regular maintenance. The read out is performed in order to ascertain that, particularly in the case of a plurality of identifiers, the associated components are all present and ready for operation. The read out may be performed optionally to access data associated with this component or these components. The data is stored in the identifier or in a separate database. After an unplanned event such as a repair or upon readout at given fixed intervals, it is always assured that only known components are present in the system.

At least one identifier of a component can be read out by software stored in memory in an internal and/or external computation device. With appropriate software, the readout operations may be controlled. The software may enables an operator to make inputs via a suitable user interface or with a software package. For example, via a suitable menu structure, the software enables the operator to choose a readout at certain intervals or upon a component replacement and the like. The software may be available on-site, for instance on a console for operating a medical diagnostic system or may be available externally or centrally, for instance in a data warehouse or at a service provider. Optionally, the readout of the identifiers may be launched directly via a choice of a menu point called "readout." Alternatively or in addition, a selection may be made for a readout of the existing identifiers or certain existing identifiers, such as the identifiers of a gradient coil system or the like, to be done at certain intervals, such as once a month, or at certain events.

In particular, mechanical and/or electrical components of the system can be detectable. If both mechanical and electrical components in the system can be detected, as is advantageously the case, then an overview of all the relevant components in the system is possible. Both electrical or electronic components may be automatically detected.

At least one component may be identified with at least one identifier based on the method of radio frequency identification and/or an optically readable identifier. The components may also be identified with more than one identifier, optionally with identifiers that are based on different readout methods. Furthermore, it is understood that medical diagnostic systems that have further identification methods are possible. In particular, care should be taken to assure that no problems as a result of the identifiers take place in the case of an identification of metal components.

The system may have at least one reader device, disposed in a cabinet or in a room in the system. The reader device is embodied for automatic readout of at least one identifier. Optionally, a plurality of reader devices may be present. For example, reader devices are fixedly installed and are provided in addition to mobile reader devices that a user carries with him. Optionally, by the use of different reader devices, it can be assured that all the identifiers, including any identifiers to be read out by touch, may be read out. For example, a fixed reader device serves the purpose of automatic readout of the most important components of the system at certain time intervals, while a mobile reader device is used to readout of only some components as needed, for instance upon a replacement.

In addition, the system may have a computation device and/or access to at least one external computation device. At least one detected component or component to be detected may be administered by software stored in memory in the internal and/or external computation device. Advantageously, the system itself has a computation device, which serves for example to allocate the read-out data to database information and to draw appropriate conclusions with a view to steps to be taken. Software in the computation device or in an external computation device may make administration of the components of the system possible. For example, for an identifier, it is possible by using software to ascertain how long the particular component can stay in the system, or when it was installed, and what maintenance intervals have to be adhered to. For that purpose, a preconfigured database may optionally be used or stored in memory in the computation device. The administration can be done automatically by the computation device or the software, or administration is guided or at least supported by an operator.

DESCRIPTION OF THE DRAWINGS

FIG. 1 shows a medical diagnostic system according to one embodiment;

FIG. 2 is a basic flow chart of one embodiment of a method for detecting installed or associated components; and FIG. 3 shows an overview of an embodiment of the hardware used to detect components.

DESCRIPTION OF EMBODIMENTS OF THE DRAWINGS

FIG. 1 shows a medical diagnostic system 1. The medical diagnostic system 1 has various components 2*a*, 2*b*, etc., which are predominantly an examination or treatment table (component 2*a*), gradient coils (2*b* and 2*g*), a field-generating magnet (2*c*), shown here only approximately, a display (2*e*), a computation device (2*f*), and a control devices (2*h* and 2*i*) in a cabinet of the system 1. The components 2*a*, 2*b*, etc. are shown in only sketched form in the drawing, without this being intended to represent the technologically exact construction.

The components 2*a*-2*i* of the medical diagnostic system 1 are each provided with at least one identifier 3*a*-3*i*, which can be read out automatically by reader devices 4*a* and 4*b*. The identifiers 3*a*-3*i* are unique in the sense that a certain component 2a-2i is associated with them. Software with a database has information on the association. The association is stored in memory in the computation device 2f.

The reader devices 4a and 4b may be based on different reading techniques, in one case an RFID technique and in the other an optical readout method. The reader devices 4a and 4b are located in a cabinet. The reader device 4a is permanently installed in this cabinet, and the reader device 4b may be removed from the cabinet of the medical diagnostic system 1 and carried around portably for optical readout of the identifiers from among the identifiers 3a-3i appropriate for the purpose.

The components 2a-2i provided with the identifiers 3a-3i are of various kinds. The components 2a-2i are not only electrical or electronic components but also mechanical components, such as the table as component 2a.

All the serialized or coded components 2a-2i of the medical diagnostic system 1 are provided with at least one identifier 3a-3i. Some of the components 2a-2i have two different identifiers, such as the gradient coil 2g, which is provided with identifiers 3g based on different methods that can be read out in the one case with the reader device 4a and in the other with the reader device 4b. The provision of more than one identifier may be appropriate particularly in the case of complex components to assure or enable reliable detection in the case of these components. A plurality of data may be stored in memory directly in the identifier so as to provide information not by way of a detour through a database, for instance in the computation device 2f.

If the medical diagnostic system 1 is now started up, for instance after repair or maintenance, the identifiers 3a-3i that are present are automatically or at least partially automatically read out with the aid of the reader devices 4a and 4b. Partially automatic readout may pertain, for example, only to replaced components from among the components 2a-2i. By the automatic readout, the components 2a-2i are detected. Optionally with the aid of software in the computation device 2f, the current data on the medical diagnostic system 1 is always present, for example with a view to a system status that conforms to what is authorized. By way of the appropriate software in a computation device 2f or externally, steps and the like pertaining to the adjustment and quality assurance may also be initiated and suitable options in this respect can be offered to an operator.

In the present case, the medical diagnostic system 1 includes still further rooms 5 and 6 in which imaging modalities 7 and 8, respectively, are present. Such further rooms 5 and 6 need not, however, necessarily be present in a medical diagnostic system 1. In the further rooms 5, 6 of the medical diagnostic system 1, whose optional status is indicated here by their being shown in dashed lines, the imaging modalities 7, 8 are likewise provided with identifiers 9, 10. In the further room 5, a cabinet 11 is also present in which a reader device 12 is located for reading out the identifier 9.

In the further room 6, an operator 13 with a mobile reader device 14 is shown. This reader device 14 serves the purpose of automatic readout of the identifier 10 by RFID technology, and of further identifiers, not shown, of the imaging modality 8. In addition, as indicated by the arrow 15, there may be an interactive data connection with the computation device 2f of the medical diagnostic system 1. The data connection allows control of the readout of the identifier 10 and other identifiers, not shown here, in the further room 6. In this case, if there is not to be recourse to the mobile reader device 14, the capability of remote readout via the reader devices 4a and 4b in the medical diagnostic system 1 is used.

The automatic readout of the identifiers 3a-3i and 9 and 10 makes it possible for a system, such as the medical diagnostic system 1, to store current status at all times in a database. The status assures the requisite safety with respect to the components 2a-2i and imaging modalities 7, 8 that are present in the system. Mistakes of the kind that can occur with manual input of data at any time are avoided by the automatic detection. If difficulties arise in detection in an exceptional case, then an error report is generated immediately by the computation device 2f or a further external computation device, not shown here, so that the identifier or the readout can be monitored with the aid of the reader devices 4a, 4b, 12, 14. The disadvantages that have existed until now with nonuniform software and detection of only a limited selection of components 2a-2i and imaging modalities 7, 8 may be avoided.

In FIG. 2, a flow chart of a method is shown. Block 16 indicates that different identifiers are located on components of a medical diagnostic system, and these identifiers are predominantly RFID identifiers. The identifiers are read out as indicated by the arrow 17. The readout is done in the local system, which is separated by the separation line 18 from the central corporate network. The automatic readout indicated by the arrow 17 serves the purpose of component detection as indicated by the circle 19. The component detection may be done upon startup of the system or as needed (on-boot or on-demand), as indicated by block 20, from which an arrow 21 points to the circle 19 for the component detection. The data from the component detection in circle 19 are stored in memory, as represented by the arrow 22, in a local database 23. The local database 23 may be an XML data base (extended markup language data base). In accordance with the arrow 24, a comparison or calibration of the new or already existing data then follows.

If based on this data comparison in accordance with arrow 24, new hardware is detected in accordance with the diamond-shaped block 25, then, as symbolized by the arrow 26, an automatic configuration, tune-up, or adjustment and a quality assurance are performed in block 27. This act can optionally be done automatically or semiautomatically with support from an operator. Using hardware, the need for such a configuration or similar steps may be pointed out, whereupon an operator performs these actions completely manually.

The new hardware detected in the diamond-shaped block 25 and the associated data, which had been recorded for instance with the identifier in block 16 or are present in the data base 23, are forwarded to the central corporate network. This data forwarding is indicated by the arrow 28. The data in accordance with arrow 28 reach an XML data warehouse, represented by block 29. From the XML data warehouse in block 29, an arrow 30 leads to block 31, which stands for the handling of the updating processes to be performed.

Within the context of the processes of the method, the components in a medical diagnostic system may be reliably detected and in particular monitored with a view to newly installed hardware. The requisite configuration steps for the new hardware or in the context of maintenance work on already existing hardware can be launched automatically. The same is true for adjustment events and events that are required for the quality assurance. Also, if desired, the data may be forwarded fully automatically to a central corporate network that has a data warehouse, so as to control the updating processes centrally.

FIG. 3 shows an overview of the hardware used for component detection in a medical diagnostic system, such as a magnetic resonance scanner. First, in a room 32, besides an RFID reader device 33, there are various components 34a-34d, which each have identifiers 35a-35d, which are RFID identifiers.

In a cabinet 36 in the medical diagnostic system, there are also a reader device 37 and various components 38a-38d. The components 38a-38d are each provided with identifiers 39a-39d, which again are RFID identifiers, which can be read out automatically by the RFID reader device 37.

A magnet chamber 40 is also present, in which in the magnetic resonance scanner to which the hardware shown is assigned, image data can be recorded. Also located in the magnet chamber 40 is an RFID reader device 41, with which the identifiers 43a-43d of the components 42a-42d in the magnet chamber 40 may be read out. Via a data line 44 with a suitable interface 45, the data read out on-boot or on-demand and associated with the components 34a-34d, 38a-38d, and 42a-42d are forwarded to a local computation device 46 that has a data base 47.

Via a wide area network, shown here at 48, there is a connection to a data warehouse 49 with a central data inventory by way of which the updating processes can be controlled or handled as needed or from which a readout of the individual components 34a-34d, 38a-38d, and 42a-42d can be brought about. The data base 47 is also, by means of the automated readout of the identifiers 35a-35d, 39a-39d, and 43a-43d, always kept reliably up to date upon component replacement or at regular intervals or upon startup of the system, so that reliable information about the components installed in the system is present.

It can thus be assured that the fundamental medical diagnostic system is in an authorized state at all times, and that the installed components are components that meet the existing safety requirements.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for detecting installed or associated components of a system, the method comprising:
reading out at least one unique identifier for each of the components;
detecting the components as a function of the unique identifiers;
identifying the components as a function of the detecting;
comparing data from the component detection to data previously stored in a memory;
forwarding at least some of the data from the component detection to a data warehouse based on the comparison between the data from the component detection and the previously stored data, the at least some of the data representing a new detected component; and
configuring, tuning-up, or adjusting the system based on the new detected component,
wherein one of the components comprises a plurality of different identifiers each associated with the one component, and
wherein reading out comprises reading out an identifier of the plurality of different identifiers based on a method of reading out.

2. The method as defined by claim 1, wherein reading out is performed by a reader device.

3. The method as defined by claim 1, wherein the at least one unique identifier of at least one of the components is read out automatically at defined times.

4. The method as defined by claim 1, wherein the at least one unique identifier of at least one of the components is read out automatically as a function of certain events.

5. The method as defined by claim 4, wherein the certain events include startup of the system and in conjunction with a repair, maintenance, replacement, or combinations thereof of the at least one component.

6. The method as defined by claim 1, wherein at least one unique identifier of one of the components is read out by software stored in the memory.

7. The method as defined by claim 1, wherein the components comprise mechanical and electrical components, and
wherein the mechanical and electrical components are detected.

8. The method as defined by claim 1, wherein at least one of the components is identified by the at least one unique identifier based on radio frequency identification.

9. The method as defined by claim 1, wherein at least one of the components is identified by the at least one unique identifier based on an optically readable identifier.

10. The method as defined by claim 1, wherein the at least one unique identifier is read out with at least one reader device located in a cabinet, in a room, or a combination thereof of the system.

11. The method as defined by claim 1, wherein at least one of the detected components is administered by software stored in the memory, the memory being in an internal computation device, an external computation device, or a combination thereof.

12. The method as defined by claim 11, further comprising retrieving further data associated with the at least one unique identifier in the memory, storing further data, or combinations thereof.

13. The method as defined by claim 12, wherein the retrieving or storing is performed by an operator or by automatic access to a database.

14. The method as defined by claim 11, further comprising:
logging, with the software, at least one of the detected components, the logging including an installation date, repairs, presence of an original part, or combinations thereof of the at least one detected component.

15. The method as defined by claim 11, further comprising:
offering options, specifications for a setting, quality assurance, or combinations thereof automatically by the software after a replacement of the at least one detected component.

16. The method as defined by claim 11, further comprising:
in the event of a later expansion of the system, the software, as a function of a readout of the unique identifiers, options, specifications for a configuration, setting, quality assurance, or combinations thereof of the at least one detected component or of the system, automatically offers or takes appropriate actions.

17. The method as defined by claim 11, wherein the software forwards data associated with the at least one detected component, data associated with the at least one unique identifier, or combinations thereof to the data warehouse.

18. The method as defined by claim 11, wherein, as a function of a data comparison with access to the software, the data warehouse connected to the software via a data connection causes configuration-specific, adjustment-specific, quality assurance-specific or combinations thereof actions for the at least one detected component or the system.

19. The method as defined by claim 1, wherein, as a function of the detection of at least one of the components, system-specific decisions are made automatically or reinforced by an operator.

20. A medical diagnostic system comprising:
a plurality of components;
identifiers for each component of the plurality of components, each component of the plurality of components being identified by at least one unique identifier that is operable to be read out by at least one reader device, the at least one unique identifier operable to be read out automatically by the at least one reader device for detecting each component, such that all components of the plurality of components are identified and detectable; and
a computer device configured to:
compare data from the component detection to data previously stored in a memory;
forward at least some of the data from the component detection to a data warehouse based on the comparison between the data from the component detection and the previously stored data, the at least some of the date representing a new detected component; and
configure, tune-up, or adjust the medical diagnostic system based on the new detected component,
wherein one component of the plurality of components comprises a plurality of identifiers each identifier of the plurality of identifiers being associated with the one component, and
wherein the at least one reader device comprises a plurality of reader devices, each reader device of the plurality of reader devices being operable to read out a different identifier of the plurality of identifiers of the one component.

21. The medical diagnostic system as defined by claim 20, wherein the at least one reader device is configured to automatically read out the identifiers.

22. The medical diagnostic system as defined by claim 21, wherein the at least one unique identifier of one component of the plurality of components is operable to be automatically read out by the at least one reader device at defined times, as a function of certain events, or combinations thereof.

23. The medical diagnostic system as defined by claim 20, wherein the at least one unique identifier of one component of the plurality of components is operable to be read out by software stored in the memory, the memory being in the computer device.

24. The medical diagnostic system as defined by claim 20, wherein the plurality of components comprises mechanical and electrical components, and
wherein the mechanical and electrical components are detectable by the at least one reader device.

25. The medical diagnostic system as defined by claim 20, wherein at least one component of the plurality of components is identified by the at least one unique identifier based on radio frequency identification, an optically readable identifier, or combinations thereof.

26. The medical diagnostic system as defined by claim 20, further comprising a cabinet or a room,
wherein the at least one reader device is disposed in the cabinet or in the room, the at least one reader device being configured for automatically reading out the at least one unique identifier.

27. The medical diagnostic system as defined by claim 20, wherein the computer device comprises software operable to control detection of the identifiers.

28. The medical diagnostic system as defined by claim 20, further comprising a magnetic resonance scanner.

* * * * *